United States Patent
Van Der Linde et al.

(10) Patent No.: US 11,123,051 B2
(45) Date of Patent: Sep. 21, 2021

(54) DEVICE WITH BENDABLE DISTAL PORTION AND SYSTEM ACTUATING THE DISTAL PORTION OF THE DEVICE

(71) Applicant: KONINKLIJKE PHILIPS N.V., Eindhoven (NL)

(72) Inventors: Franciscus Reinier Antonius Van Der Linde, Schijndel (NL); Cornelis Gerardus Maria De Haas, Nuenen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 47 days.

(21) Appl. No.: 16/247,485

(22) Filed: Jan. 14, 2019

(65) Prior Publication Data
US 2019/0216448 A1 Jul. 18, 2019

(30) Foreign Application Priority Data

Jan. 15, 2018 (EP) ..................... 18151645

(51) Int. Cl.
| A61B 17/00 | (2006.01) |
| A61B 34/20 | (2016.01) |
| A61M 25/01 | (2006.01) |
| A61B 1/005 | (2006.01) |
| A61B 34/00 | (2016.01) |
| A61B 34/30 | (2016.01) |

(52) U.S. Cl.
CPC ...... *A61B 17/00234* (2013.01); *A61B 1/0052* (2013.01); *A61B 1/0055* (2013.01); *A61B 34/20* (2016.02); *A61B 34/70* (2016.02); *A61M 25/0136* (2013.01); *A61B 34/71* (2016.02); *A61B 2017/00022* (2013.01); *A61B 2017/00221* (2013.01); *A61B 2017/00327* (2013.01); *A61B 2034/301* (2016.02); *A61M 25/0147* (2013.01); *A61M 2025/0166* (2013.01)

(58) Field of Classification Search
CPC .......... A61M 25/0133; A61M 25/0136; A61M 25/0147; A61B 2017/2905; A61B 1/0055; A61B 1/0056; A61B 2034/301; A61B 34/70; A61B 34/71; A61B 1/0051; A61B 1/0052; A61B 1/0057
See application file for complete search history.

(56) References Cited

U.S. PATENT DOCUMENTS

| 6,487,545 | B1 | 11/2002 | Wical |
| 6,544,215 | B1 | 4/2003 | Bencini |
| 8,105,350 | B2 * | 1/2012 | Lee .................... A61B 1/00071 606/205 |
| 9,247,990 | B2 | 2/2016 | Sablan |

(Continued)

*Primary Examiner* — Wade Miles

(57) ABSTRACT

A device with bendable distal end of its elongate body and a system actuating the distal portion of the device is disclosed. A rigid elongate member fixedly attached to a distal portion of a grip structure and forming a pathway for pull-wires, can be manipulated by a control organ, such that an angular displacement of the rigid elongate member within the hollow grip structure with respect to the distal portion of the grip generates bending of the distal portion of the elongate body. The device may further comprise a mechanism for immobilizing the rigid elongate member with respect to the grip in a selected position, such that the bent distal portion of the elongate body remains fixed in the selected position.

14 Claims, 8 Drawing Sheets

(56) References Cited

U.S. PATENT DOCUMENTS

| | | | |
|---|---|---|---|
| 2010/0228235 A1 | 9/2010 | Lee | |
| 2010/0286480 A1* | 11/2010 | Peine | A61B 17/2909 |
| | | | 600/131 |
| 2011/0213347 A1 | 9/2011 | Lee | |
| 2011/0295242 A1* | 12/2011 | Spivey | A61B 17/068 |
| | | | 606/1 |
| 2016/0184038 A1* | 6/2016 | Denissen | B25J 9/1633 |
| | | | 606/130 |
| 2016/0338760 A1* | 11/2016 | Houser | H02J 7/025 |
| 2017/0296178 A1* | 10/2017 | Miller | A61B 5/0261 |
| 2017/0333679 A1 | 11/2017 | Jiang | |

* cited by examiner

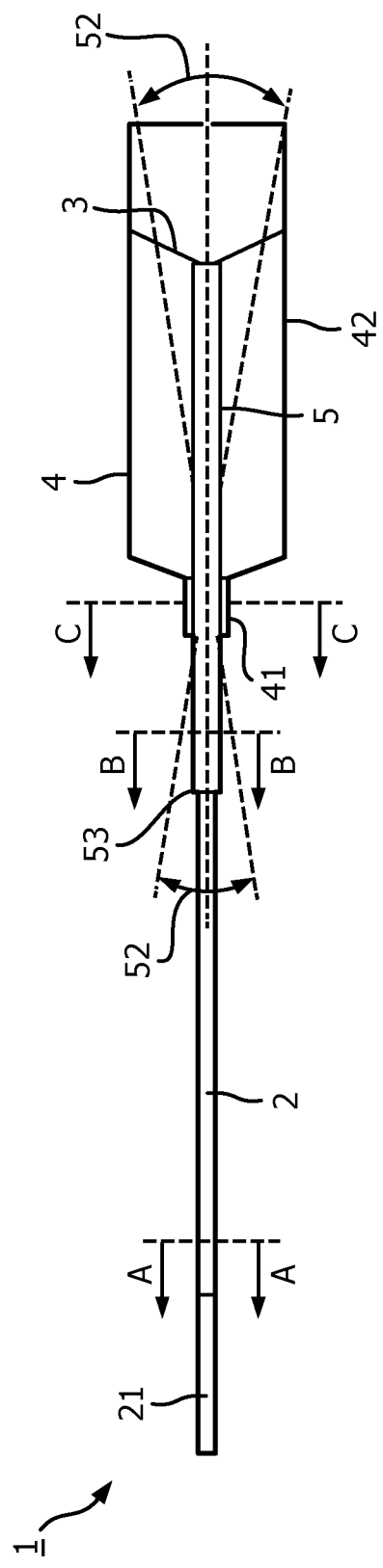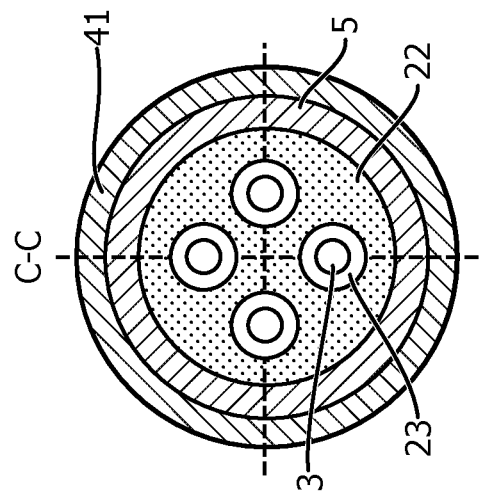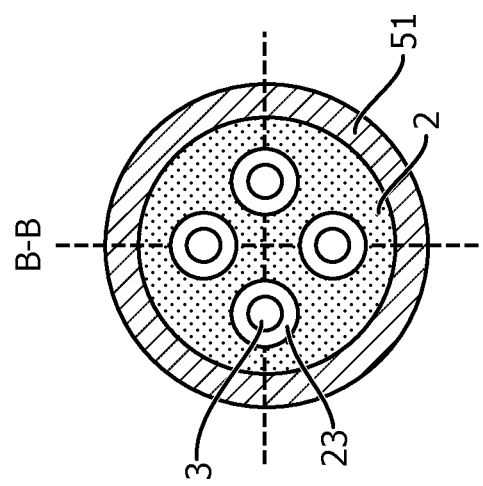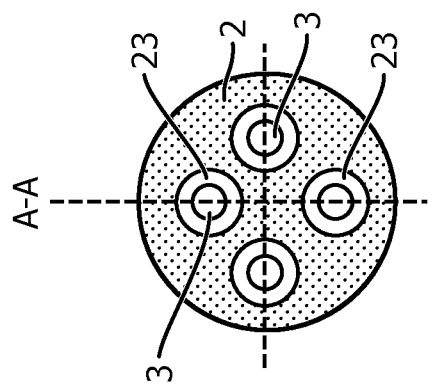
FIG. 2A
FIG. 2B
FIG. 2C
FIG. 2D

DEVICE WITH BENDABLE DISTAL PORTION AND SYSTEM ACTUATING THE DISTAL PORTION OF THE DEVICE

FIELD OF THE INVENTION

The invention relates to devices with bendable distal end and system actuating the distal end of the devices.

BACKGROUND OF THE INVENTION

Medical devices comprise pull-wires within their elongate body for enabling bending of their distal portion. The pull-wires extend from a handgrip at the proximal portion of the elongate body to the distal flexible portion of the medical device, and the bending of the distal portion is controlled by a knob on the outside of the handgrip that is connected through a mechanism, located inside the handgrip, to the proximal portion of the pull-wires. Such medical devices are often called steerable medical devices, as bending of their distal portion allows steering of their distal end through a vessel network of a patient's body to a designated location for diagnosis and/or treatment purposes. Examples of medical device with steering mechanism using pull-wires are disclosed in U.S. Pat. No. 6,485,455 B1 and US2017/0333679 A1. Failure of the moving parts of the mechanism, usually comprising a rotatable cam or a pulley, or snapping of the pull-wires from the mechanism, results in inability to use the steering functionality of the medical device.

It remains a need to reduce complexity of the mechanism responsible for controlling the bending of the distal end of the medical device, thereby increasing the reliability of the medical device, especially for multiple clinical uses.

SUMMARY OF THE INVENTION

It is an object of the present invention to reduce the complexity of the mechanism responsible for controlling the bending of the distal end of an elongate device.

According to a first aspect of the invention an elongate device is provided with bendable distal end, comprising:

an elongate body having a distal portion, a proximal portion and a lumen;

a pull-wire located within the lumen, extending from the distal portion to the proximal portion of the elongate body and fixedly attached to the distal portion eccentrically with respect to a longitudinal axis of the elongate body;

a hollow grip structure connected to the proximal portion of the elongate body;

a rigid elongate member fixedly attached to a distal portion of the grip and forming a pathway for the pull-wire, wherein the pull-wire extends proximally from the rigid elongate member and is fixedly attached to a wall of the grip structure, wherein the rigid elongate member is configured for angular displacement within the hollow grip structure with respect to the distal portion of the grip;

a control organ for influencing the angular displacement of the rigid elongate member.

The complexity of the mechanism responsible for controlling the bending of the distal end of the medical device is reduced, thereby increasing the reliability of the medical device, especially for multiple clinical uses. The number of movable components of the steering mechanism is reduced, which reduces the chances for failure.

In an embodiment of the invention the device comprises two pull-wires located at opposite sides of a diagonal through the longitudinal axis of the elongate body, and the rigid elongate member is configured for angular displacement in a longitudinal plane comprising its longitudinal axis. This embodiment enables bidirectional bending of the distal portion of the device, particularly to both sides of the longitudinal axis of the elongate body.

In a further embodiment of the invention the device comprises three or four pull-wires located equidistant from each other and equidistant from the longitudinal axis of the elongate body in a plane transversal to the longitudinal axis of the elongate body. This embodiment enables omnidirectional bending of the distal portion of the device, meaning that the bending of the distal end can be controlled to any angle radial to the longitudinal axis of the elongate body.

In yet a further embodiment of the invention the diameter of the pull-wire is in the range of 0.025-0.15 mm and the diameter of the elongate body is in the range of 0.55-1.5 mm. The dimensions of the components allow miniaturization of a device, in particular for manufacturing of micro-catheters for use in coronary or cerebral vasculature.

In an embodiment of the device according to the invention a distal portion of the grip extends along a predetermined length of the rigid elongate member, the distal portion of the grip is configured to follow the angular displacement of the rigid elongate member and to allow movement of the distal portion of the grip with respect to a proximal main body of the grip. The distal portion and the proximal main body of the grip can be a single-body grip of a particular material, for example plastic. The motion of the distal portion of the grip with respect to the main body of the grip creates a resistance to the motion of the control organ that influences the angular displacement of the rigid elongate member, thereby when the control organ is released, the rigid elongate member regains its neutral position causing the distal end of the elongate body to retrieve its neutral position.

In a further embodiment of the invention the inner cross section of the distal portion of the grip is configured for press-fitting the rigid elongate member, and the inner cross section of the main body is at least three times the inner cross section of the distal portion of the grip. The difference between the inner cross sections is for controlling the angular displacement stroke of the rigid elongate member, and thereby the bending radius of the distal portion of the elongate body. Press-fitting the rigid elongate member within the distal portion of the grip creates the benefit of a good seal at the distal end of the grip, without use or extensive use of adhesives.

In an embodiment, the control organ is connected to the rigid elongate member, and it is operable from an outer side of the grip, whereby the physicians can control the bending of the distal end of the device in a conventional way. Alternatively, the control organ can be an extension of the rigid elongate member distal to the grip structure. The benefit is that no additional opening is necessary on the body of the grip for accommodating the control organ that needs to connect to the rigid elongate member.

In an embodiment, the distal portion of the elongate body comprises a sensor connected to a control unit located within the grip. The sensor, which may be an ultrasound sensor, a pressure sensor, a flow sensor, a pH sensor, a temperature sensor, an optical imaging sensor, a sensor for measuring electrical signals or a combination of them, is controlled by the control unit located within the grip, wherein the control unit is energized by an integrated internal energy source or an external energy source.

In a further embodiment of the device the control unit is configured for wireless communication with an external processing unit for transmitting measurement information from the sensor to the external control unit. The benefit of the embodiment is that no connection cables are required between the device and the external processing unit for transfer of measurement information.

In yet a further embodiment of the device, the elongate body, the grip, the connection of the elongate body to the grip and to the rigid elongate member are configured to form a closed system, whereby the device is leak-tight to liquids. The device can easily be made leak-tight to liquids due to the fact that the grip requires only one opening for connection of the elongate body to the grip through the rigid elongate member, particularly at the distal end of the grip, where the rigid elongate member is either press-fit within the distal portion of the grip or alternatively glued. The angular displacement can be controlled by the displacement of the distal extension of the rigid member with respect to the proximal main body of the grip. The sensors optionally located at the distal portion of the elongate body and connected to the control unit within the grip, wherein the control unit is configured for wireless transmission of the measurement information to an external processing unit, also does not require additional openings on the grip. As result, a device leak-tight to liquid is easily obtainable, which is advantageous for steerable devices for multiple clinical uses, where multiple reprocessing such as cleaning and/or sterilization of the device may involve liquids. Additionally, the circumstances of the clinical use of the device may involve body-liquids, e.g. blood, and the prevention of penetration of body-liquids in the device is important for devices for multiple uses.

In an embodiment of the invention the device comprises a mechanism for immobilizing the rigid elongate member with respect to the grip in a selected position. Physicians often need to leave devices navigated to a target location within the body, in order to advance additional devices to the same location for diagnostic or for treatment purposes. Therefore, it is beneficial to leave the distal portion of the device in an immobilized position with respect to the structure of the anatomy, e.g. the distal portion of the device bent in a branch of a blood vessel according to the curvature of the branch, such that the distal portion of the device does not cause unnecessary stress to the blood vessel wall. The device with the fixable bending of the distal portion of the elongate body may be a guidewire, a diagnostic catheter or a treatment catheter.

In an embodiment, the mechanism comprises:

a friction disc fixedly attached to the proximal portion of the rigid elongate member;

a first structure fixed within the hollow grip at a position proximal to the friction disc;

a second structure movable within the hollow grip and located distal to the friction disc;

a second control organ connected to the movable second structure and operable from the outside of the wall of the grip. The second control organ may be a lever or a button that is movable with respect to the grip and which causes the second structure to axially translate within the grip to press onto the friction disc and to press the friction disc onto the first structure, thereby immobilizing the rigid elongate member. The motion of the second organ may combine rotation with translation to achieve the desired effect.

In another aspect of the invention a system is provided, comprising the device according to the invention and an apparatus configured to:

clasp the grip and the control organ; and provide relative motion of the control organ with respect to the grip based on a predetermined roadmap. The advantage is that the steering of the distal portion of elongate body is automatized based on a predetermined roadmap, which may be for navigation through a vessel network to a target location for diagnostic purposes such as diagnostic of stenosis in coronary or cerebrovascular vessel, or for treatment of an anatomical organ such as a heart, wherein ablations are required on multiples sites for treating cardiac arrhythmia.

In a further embodiment of the system the predetermined roadmap is based on extracorporeal imaging of a vessel system and/or an anatomical organ in a body. Imaging of anatomical structures may be performed by various well established techniques such as: radiological angiography (RA) including computed tomography angiography, magnetic resonance angiography (MRA) or ultrasound imaging (UI). For the respective imaging modalities also contrast agents are available for enhancing the features of the blood vessel system, for instance radiological contrast agent for RA, a gadolinium-based substance for MRA, echogenic contrast agent comprising microbubbles for extracorporeal UI. The information of the vessel system and/or the anatomical organ is received by the apparatus, and a processor of the apparatus computes the required movements of the control organ with respect to the grip, so that a target location within the vessel system can be reached, or multiple locations in an anatomical organ can be reached in a sequence for treatment, then subsequently the processor controls two arms of the apparatus that hold the control organ and the grip for automatically navigating the distal portion of the elongate body to the predetermined target locations.

These and other aspects of the invention will be apparent from and elucidated with reference to the embodiments described hereinafter.

BRIEF DESCRIPTION OF THE DRAWINGS

In the following drawings:

FIGS. 2A-2D illustrate schematically and exemplarily a second embodiment of the device according to the invention.

DETAILED DESCRIPTION OF EMBODIMENTS

Figure 1A:
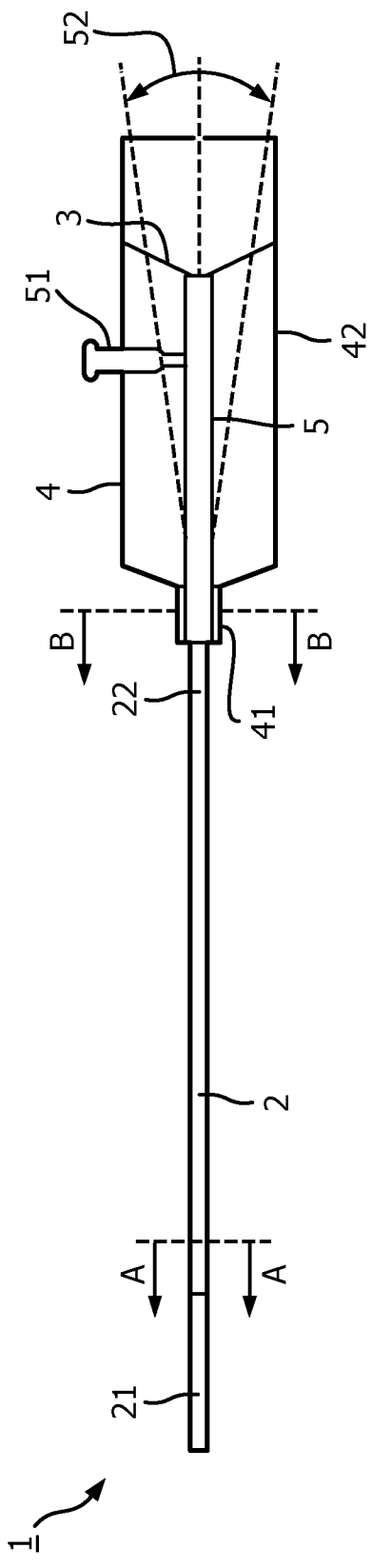
FIGS. 1A-1C illustrate schematically and exemplarily a first embodiment of the device according to the invention.
Figure 1C:
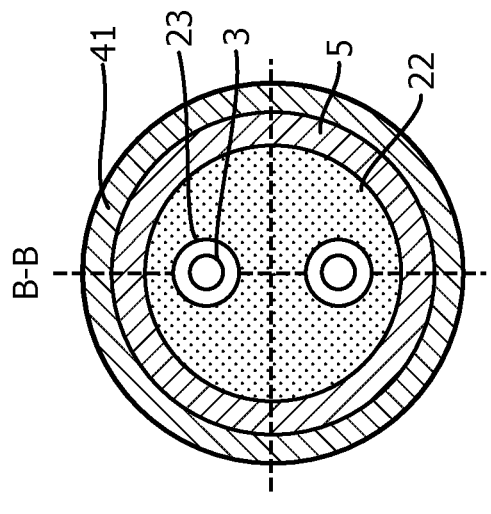
Figure 1B:
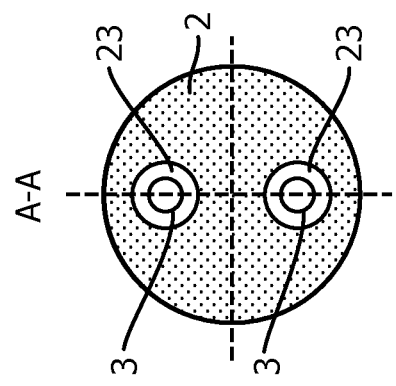

FIGS. 1A-1C schematically and exemplarily show a first embodiment of the elongate device with bendable distal end according to the invention. The device 1 comprises: an elongate body 2 with a distal portion 21, a proximal portion 22 and having a lumen 23; a pull-wire 3 located within the lumen 23, extending from the distal portion 21 to the proximal portion 22 of the elongate body 2 and fixedly attached in the distal portion 21 eccentrically to the longitudinal axis of the elongate body 2; a hollow grip structure 4 connected to the proximal portion 22 of the elongate body 2; a rigid elongate member 5 fixedly attached to a distal portion 41 of the grip 4 and forming a pathway for the pull-wire 3, wherein the pull-wire 3 extends proximally from the rigid elongate member 5 and is fixedly attached to a wall of the grip structure 4, wherein the rigid elongate member 5 is configured for angular displacement 52 within the hollow grip 4 structure with respect to the distal portion 41 of the grip 4; a control organ 51 for influencing the angular displacement 52 of the rigid elongate member 5. The grip structure 4 is illustrated in the side view of the device in FIG. 1A. For the sake of clarity the grip is illustrated as it would be made of a transparent material, in order to allow depiction of the elements that are located within the hollow grip. The grip structure may be made of plastic or metal, in particular of thermoplastic material or alloys of light metals. The rigid elongate member can be made of hypotube, in particular of stainless steel. The elongate body of the device may be made of thermoplastic material, in particular Pebax for medical devices. The distal portion 21 of the elongate body 2 may have a different stiffness than the middle section, for allowing a different bending profile of the distal portion of the elongate body with respect to the middle section. In clinical practice the distal portion 21 of the elongate body 2 has a lower hardness than the middle section of the elongate body, which can be obtained for example by heat-fusing Pebax sections of different hardness grades. The control organ may be a lever or a button connected to the rigid elongate member 5, which can be manipulated by a physician from the outer side of the grip 4 in order to control the angular displacement of the rigid elongate member, resulting in a bending of the distal portion 21 of the elongate member 2.

FIG. 1B shows a cross section A-A of the elongate body of the embodiment illustrated in FIG. 1A, wherein two lumens 23 are present, and in which two pull-wires 3 extend from the distal portion 21 of the elongate body 2. The distal ends of the pull wires are fixedly attached with respect to the elongate body in its distal portion and the proximal ends of the pull-wires are fixedly attached to the wall of the grip structure 4. The device comprises two pull-wires located at opposite sides of a diagonal through the longitudinal axis of the elongate body. This enables bidirectional bending of the distal portion of the device, particularly to both sides of the longitudinal axis of the elongate body. The effect is achieved by setting a position of the rigid elongate member 5 in a selected particular angle with respect to the longitudinal axis of the grip structure 4 by a movement of the control organ 51, upon which the proximal end of the rigid elongate member 5 tenses one of the pull-wires 3, such that the length of that particular pull-wire 3 extending proximally from the rigid elongate member becomes longer and therefore the length of that particular pull-wire extending distally to the proximal end of the rigid elongate member 5 becomes shorter. Since the pull-wire 3 is fixedly attached to the distal portion 21 eccentrically with respect to the longitudinal axis of the elongate body 2, the shortening of the pull-wire 3 distal to the proximal end of the rigid elongate member 5 results in bending of the distal portion of the elongate body. The direction of bending of the distal portion of the elongate body is defined by the side to which the particular pull-wire, undergoing a tension due to the action of the rigid elongate member, is attached with respect to the longitudinal axis of the elongate body. The attachment of the pull-wire in the distal portion of the elongate body may be accomplished by means of a ring fixed into the distal portion of the elongate body, and to which the distal end of the pull-wire is welded or soldered. Alternatively, the distal end of the pull-wire can be attached to the distal portion by local thermal reflow of the distal portion of the elongate body after insertion of the distal end of the pull-wire. Optionally, the distal end of the pull-wire may comprise a structure (e.g. hook, loop) for supporting fixation when encapsulated in the material of the distal portion of the elongate body after local thermal reflow.

Although the pull-wires in FIGS. 1A-1C are located in separate lumens, in alternative embodiment the pull-wires may be located within a single lumen. In a further alternative embodiment there is only one pull-wire in a single lumen of the elongate body, of which a distal end is fixedly attached eccentrically to the elongate body. The device enables unidirectional bending of the distal portion of the elongate body, and the neutral position of the elongate body is regained by the resilience of the material of the elongate body after manipulation of the control organ 51 is terminated. In yet a further alternative embodiment the device may comprise three or four pull-wires located equidistant from each other and equidistant from the longitudinal axis of the elongate body in a plane transversal to the longitudinal axis of the elongate body. The bending of the distal portion of the elongate body in all of the alternative embodiments is achieved in the manner described for the embodiment illustrated in FIGS. 1A-1C, by tensing at least one of the pull-wires by the angular displacement of the rigid elongate member controlled by the control organ.

FIG. 1C shows a cross section B-B of the device illustrated in FIG. 1A. The proximal portion 22 of the elongate body 2, comprising the lumens 23 for hosting the pull-wires 3, is surrounded by the rigid elongate member 5. The proximal portion 22 of the elongate body 2 may extend partially or fully within the rigid elongate member 5, and the elongate body is fixedly attached to the rigid elongate member either by press-fitting, by an adhesive or by a combination of the two. The distal portion 41 of the grip 4 surrounds the rigid elongate member 5, and the inner cross section of the distal portion of the grip allows attachment to the rigid elongate member either by press-fitting, by an adhesive or by a combination of the two.

In the embodiment of the device illustrated in FIGS. 1A-1C the rigid elongate member 5 forms a pathway for the pull-wires 3, which extend proximally from the rigid elongate member 5 and are fixedly attached to a wall of the grip structure 4. This can be achieved by mechanical attachment of the pull-wires to the grip for instance with screws or by inclusion of the proximal ends of the pull-wires within the structure of the grip during forming of the grip structure from a thermoplastic material. The pull-wires are not restricted and not fixed along the lumen of the elongate body and along the rigid elongate member, as it is illustrated in the cross sections of FIGS. 1B and 1C, thus only the distal and proximal ends of the pull-wires are fixed with respect to the distal portion of the elongate body and the proximal main body 42 of the grip structure, respectively. The inner cross section of the main body 42 of the grip structure 4 is at least three times the inner cross section of the distal portion 41 of the grip, in order to allow sufficient stroke for angular displacement 52 of the rigid elongate member 5 within the proximal main body 42 of the hollow grip 4 with respect to the distal portion 41 of the grip 4. The distal portion of the grip extends along a predetermined length of the rigid elongate member, and follows the angular displacement of the rigid member. In this embodiment the grip structure is configured to allow movement of the distal portion of the grip with respect to the proximal main body of the grip. The distal portion and the proximal main body of the grip can be a single-body grip of a particular material, for example plastic. By varying the thickness of the wall along the grip structure, e.g. thin wall at the proximal portion of the grip and thick wall for rigidity of the proximal main body of the grip, the distal portion of the grip allows movement with respect to the proximal main body of the grip for a single-body grip structure. The motion of the distal portion of the grip with respect to the proximal main body of the grip creates a resistance to the motion of the control organ that influences the angular displacement of the rigid elongate member, thereby when the control organ is released, the rigid elongate member regains its neutral position causing the distal end of the elongate body to retrieve its neutral position. Alternatively, the distal portion 41 of the grip 4 may be articulated with respect to the proximal main body of the grip, and the grip can be made of multiple parts. For both alternatives, the portion of the grip that connects the distal portion of the grip 41 to the proximal main body of the grip 42 acts as fulcrum for the rigid elongate member, with respect to which the angular displacement is achieved by manipulating the rigid elongate member 5 through operation of the control organ 51. As result, the angle formed by the longitudinal axis of the rigid elongate member 5 with respect to the longitudinal axis of the proximal main body 42 of the grip structure 4 can be changed through manipulation of the rigid elongate member 5 by the control organ 51, which generates bending of the distal portion 21 of the elongate body 2 directly related to the angle. When the longitudinal axes of the rigid elongate member 5 and the proximal main body 42 of the grip structure 4 coincide, then the distal portion 21 of the elongate body 2 is in neutral position.

FIGS. 2A-2D schematically and exemplarily show a second embodiment of the elongate device with bendable distal end according to the invention, wherein the components similar to the already discussed first embodiment are referenced with identical numbers. The second embodiment of the device comprises four pull-wires located equidistant from each other and equidistant from the longitudinal axis of the elongate body in a plane transversal to the longitudinal axis of the elongate body, as it can be seen on FIGS. 2B-2D. In alternative embodiments the device may comprise one pull-wire eccentric to the longitudinal axis of the elongate body, or any other variation of multiple pull-wires, e.g. two, three, six, eight, located equidistant from each other and equidistant from the longitudinal axis of the elongate body in a plane transversal to the longitudinal axis of the elongate body. The control organ is an extension of the rigid elongate member 5 distal to the grip structure 4, as it can be seen also in the cross section B-B on FIG. 2C. The distal portion 53 of the rigid elongate member 5 extending distally from the distal portion 41 of the grip structure 4 serves as control organ for manipulating the rigid elongate member with respect to the proximal main body 42 of the grip structure 4, in order to achieve the angular displacement of the rigid elongate member. The portion of the grip that connects the distal portion of the grip 41 to the proximal main body of the grip 42 acts as fulcrum for the rigid elongate member 5, with respect to which the angular displacement is achieved by manipulating the rigid elongate member 5 through the control organ, being in this case the distal extension of the rigid elongate member. The attachment and connection of components for the second embodiment and which are referenced identically to the first embodiment illustrated in FIGS. 1A-1C, may be achieved in identical or similar ways.

Figure 3A:
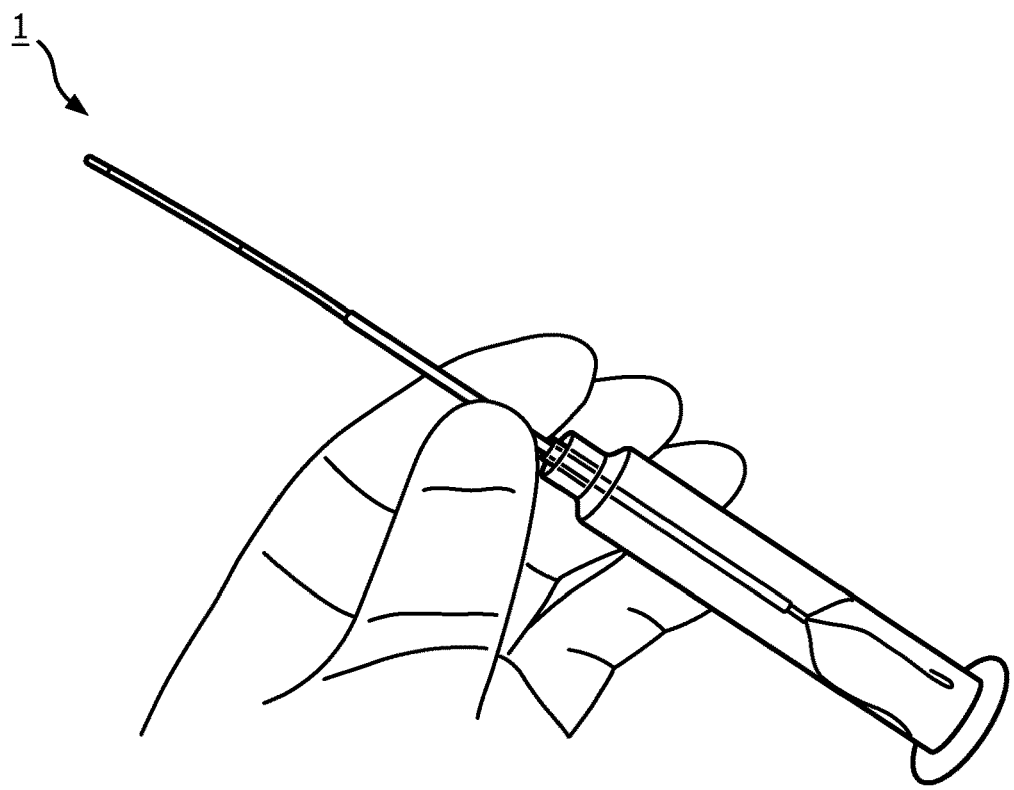
FIGS. 3A and 3B are photographs of the second embodiment of the device according to the invention.
Figure 3B:
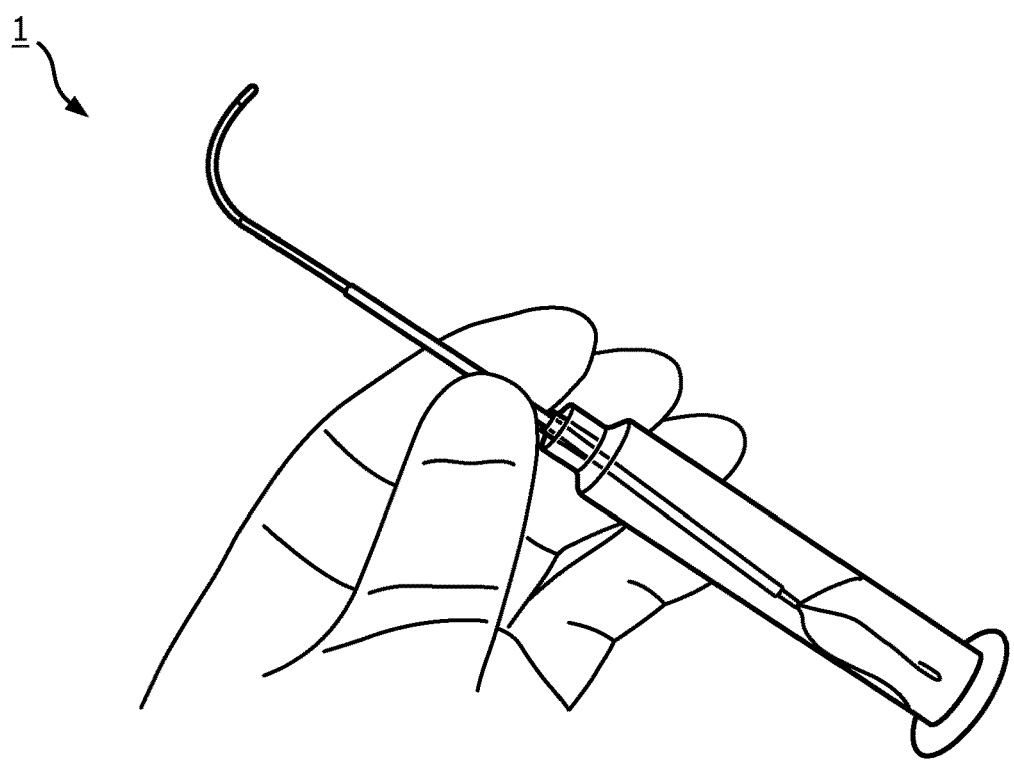

Photographs demonstrating the functional operation of the second embodiment of the device are shown in FIGS. 3A and 3B. In FIG. 3A the distal portion of the elongate body is in neutral position, whereas by manipulating the distal extension of the rigid elongate member with respect to the proximal main body of the grip structure in FIG. 3B generates bending of the distal portion of the elongate body. The length of the elongate body may be in the range of 20 cm to 200 cm, depending on the clinical application. For coronary and peripheral applications the length of the elongate body is preferably between 120-200 cm. For microcatheters according to any of the embodiments of the device, and which are used in cerebrovascular or coronary applications, the diameter of the pull-wire can be in the range of 0.025-0.15 mm and the diameter of the elongate body can be in the range of 0.55-1.5 mm. For peripheral applications or cardiac applications involving treatment of anomalies of any of the cardiac chambers, the diameter of the elongate body may be up to 4 mm and the diameter of the pull-wire may be up to 0.25 mm. The angle formed by the longitudinal axis of the rigid elongate member 5 with respect to the longitudinal axis of the proximal main body 42 of the grip structure 4 can be changed through manipulation of the distal portion 53 of the rigid elongate member 5 with respect to the proximal main body 42 of the grip 4, which generates bending of the distal portion 21 of the elongate body 2 directly related to the angle. When the longitudinal axes of the rigid elongate member 5 and the proximal main body 42 of the grip structure 4 coincide, then the distal portion 21 of the elongate body 2 is in the neutral position.

Figure 4:
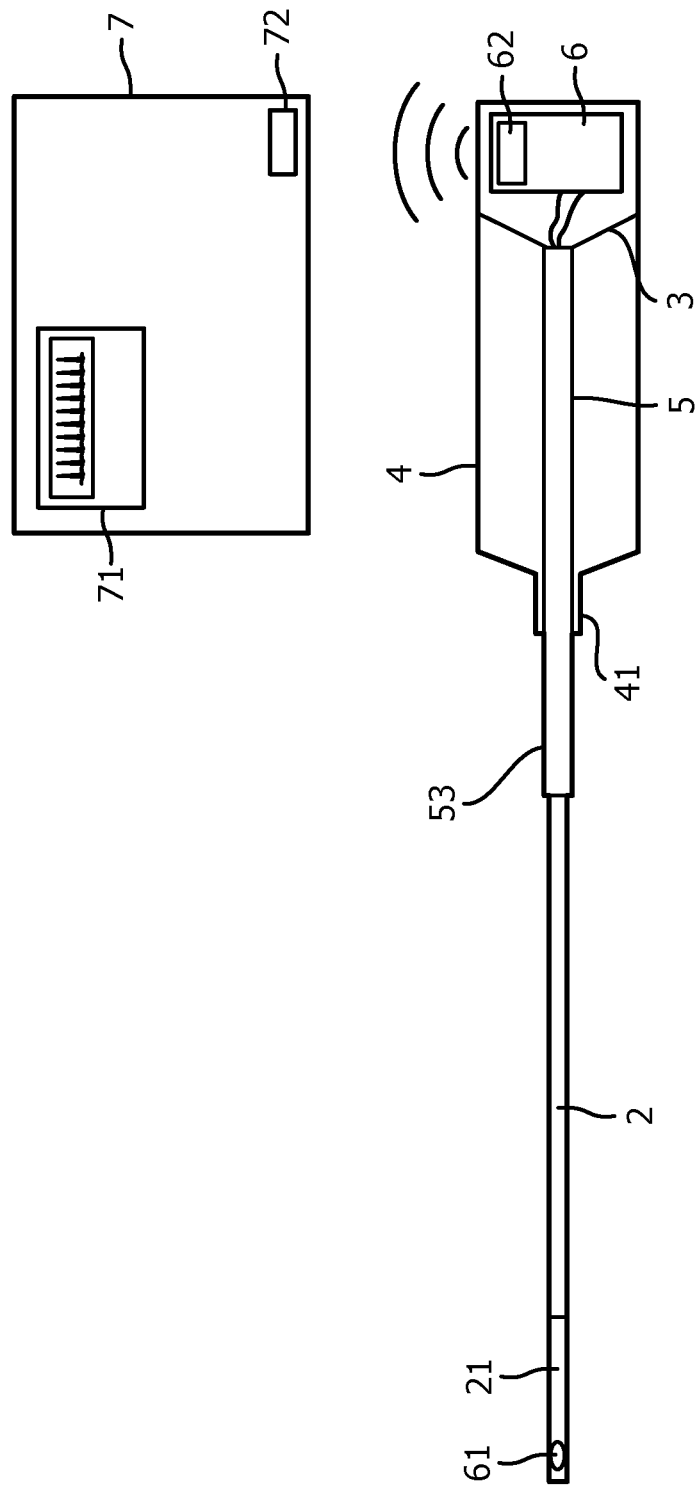
FIG. 4 is a schematic and exemplary illustration of a third embodiment of the device according to the invention.

Any of the embodiments of the device may comprise a sensor 61 on the distal portion 21 of the elongate body 2, as shown if FIG. 4. The sensor 61 is connected to a control unit 6 located within the grip 4. The sensor, which may be an ultrasound sensor, a pressure sensor, a flow sensor, a pH sensor, a temperature sensor, an optical imaging sensor, a sensor for measuring electrical signals or a combination of them, is controlled by the control unit 6 located within the grip, wherein the control unit is energized by an integrated internal energy source or an external energy source. The control unit 6 may comprise a signal emitter/receiver 62 configured for wireless communication with an emitter/receiver 72 of an external processing unit 7 for transmitting measurement information obtained by the sensor 61. The benefit of the embodiment is that no connection cables are required between the device and the external processing unit for transfer of measurement information. The wireless communication also enables external control of the measurement parameters of the sensor if and when required. The external processing unit is configured to output the measurement signals to a display 71. The display may be integrated with the external processing unit, or alternatively it may be a separate unit.

The elongate body, the grip structure, the connection of the elongate body to the grip and to the rigid member are configured to form a closed system, whereby the device is leak-tight to liquids. The device can easily be made leak-tight to liquids due to the fact that the grip requires only one opening for connection of the elongate body to the grip through the rigid elongate member, particularly at the distal end of the grip, where the rigid elongate member is either press-fit within the distal portion of the grip or alternatively is glued. Alternatively or additionally, the material of the grip may be of a plastic that upon local heating of its distal portion shrinks onto the rigid elongate member. Any of these attachment techniques provide a leak-tight sealing of the grip. The angular displacement of the rigid elongate member can be controlled by the displacement of the extension of the rigid elongate member distal to the distal portion of the grip structure with respect to the proximal main body of the grip. The sensors optionally located at the distal portion of the elongate body and connected to the control unit within the grip, wherein the control unit is configured for wireless transmission of the measurement information to an external processing unit, also does not require additional openings on the grip. As a result, a device that is leak-tight to liquids can easily be obtained, which is advantageous for steerable devices for multiple clinical uses, where multiple reprocessing such as cleaning and/or sterilization of the device may involve liquids. Additionally, the circumstances of the clinical use of the device may involve body-liquids, e.g. blood, and the prevention of penetration of body-liquids in the device is important for devices for multiple uses.

Although the transversal profiles of the components of the devices illustrated schematically and exemplarily in the FIGS. are circular, in alternative embodiments any of the components may have transversal profile according to a different geometrical form, such as oval, square, rectangular, hexagonal, etc.

Figure 5A:
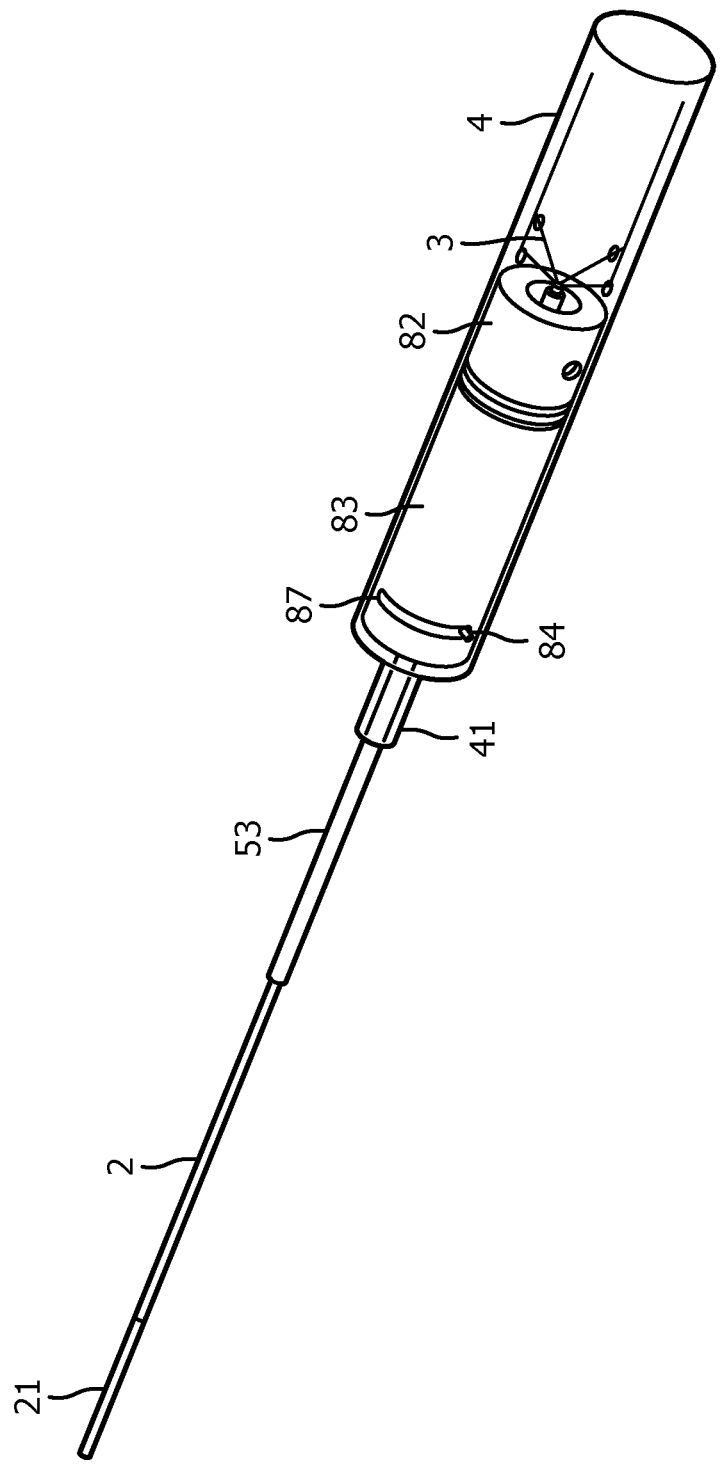
FIGS. 5A-5C illustrate schematically and exemplarily a fourth embodiment of the device according to the invention.
Figure 5B:
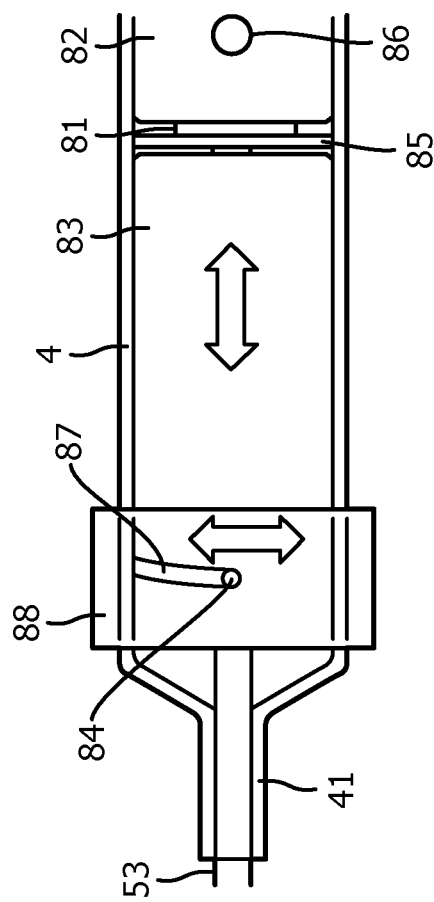
Figure 5C:
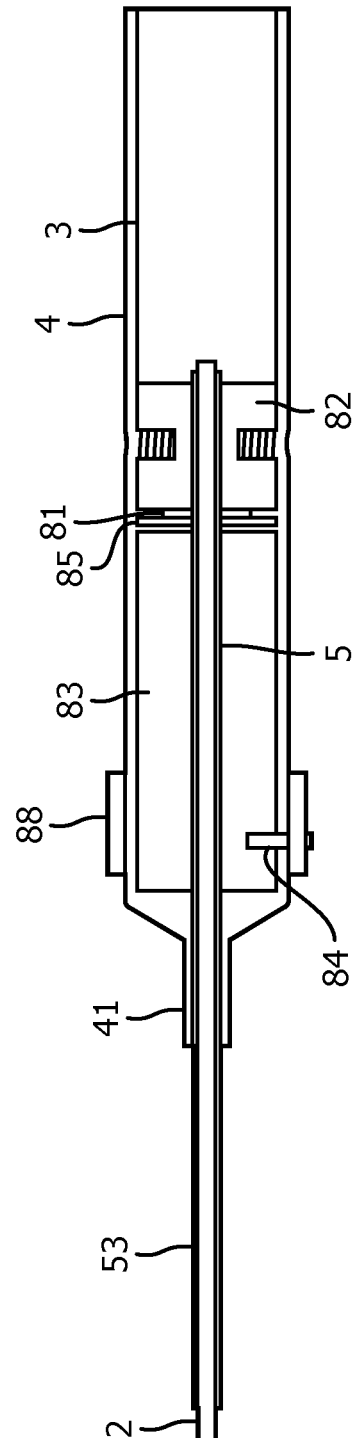

In any of the embodiments of the device according to the invention the grip may accommodate a mechanism for immobilizing the rigid elongate member with respect to the proximal main body of the grip in a selected position. Physicians often need to leave devices, e.g. guidewire, diagnostic catheter or treatment catheter, navigated to a target location within the body for advancing additional devices to the same location for diagnostic or for treatment purposes. Therefore, it is beneficial to leave the device in an immobilized position with respect to the structure of the anatomy, e.g. in a branch of a blood vessel. The mechanism able to immobilize the rigid elongate member with respect to the proximal main body of the grip in a selected position may also be called braking mechanism. A schematic and exemplary embodiment of such a braking mechanism is shown is FIGS. 5A-5C, which comprises a friction disc 81 fixedly attached to the proximal portion of the rigid elongate member 5; a first structure 82 fixed within the hollow grip 4 at a position proximal to the friction disc 81; a second structure 83 movable within the hollow grip 4 and located distal to the friction disc 81; a second control organ 84 connected to the movable second structure 83 and operable from the outer side of the grip 4. The second control organ 84 may be a lever or a button that is movable with respect to the grip and which causes the second structure 83 to axially translate within the grip to press onto the friction disc 81 and to press the friction disc 81 onto the first structure 82, thereby immobilizing the rigid elongate member. The motion of the second control organ 84 may combine rotation with translation to achieve the desired effect, such as illustrated in FIG. 5B. Both, the first structure 82 and the second structure 83 are hollow and the rigid elongate member 5 passes through their lumens, to allow the proximal ends of the pull-wires 3 to be fixedly attached to the proximal main body 42 of the grip structure 4 proximal to the first structure 82 of the immobilizing mechanism. The inner diameters of the first and second structures are dimensioned to allow angular movement of the rigid elongate member within the desired stroke, as can be observed in FIG. 5C. The diameter of the friction disc is smaller than the inner diameter of the proximal main body of the grip, and since it is fixedly attached to the rigid elongate member, its diameter limits the stroke of the angular displacement of the rigid elongate member. Additionally, a washer 85 that is not attached to the rigid elongate member 5 may be placed between the first structure 82 and the friction disc 81, and/or between the friction disc 81 and the second structure 83. The inner diameter of the washer 85 is dimensioned to allow angular movement of the rigid elongate member within the desired stroke, and its outer diameter to allow free movement of the washer within the proximal main body of the grip structure. The first structure 82 may be fixedly attached to the grip structure 4 by means of screw 86, by adhesive, or it may be part of the grip structure formed as a step with smaller inner diameter with respect to the inner diameter of the proximal main body of the grip. The second control organ 84, which may be regarded as a brake control element for immobilizing the rigid elongate member 5 in a desired position defined by a selected angular position of the rigid elongate member, projects through a slit within the grip structure or through a slit 87 of an annular brace 88 fixedly attached to the outer surface of the grip structure 4.

Figure 6:
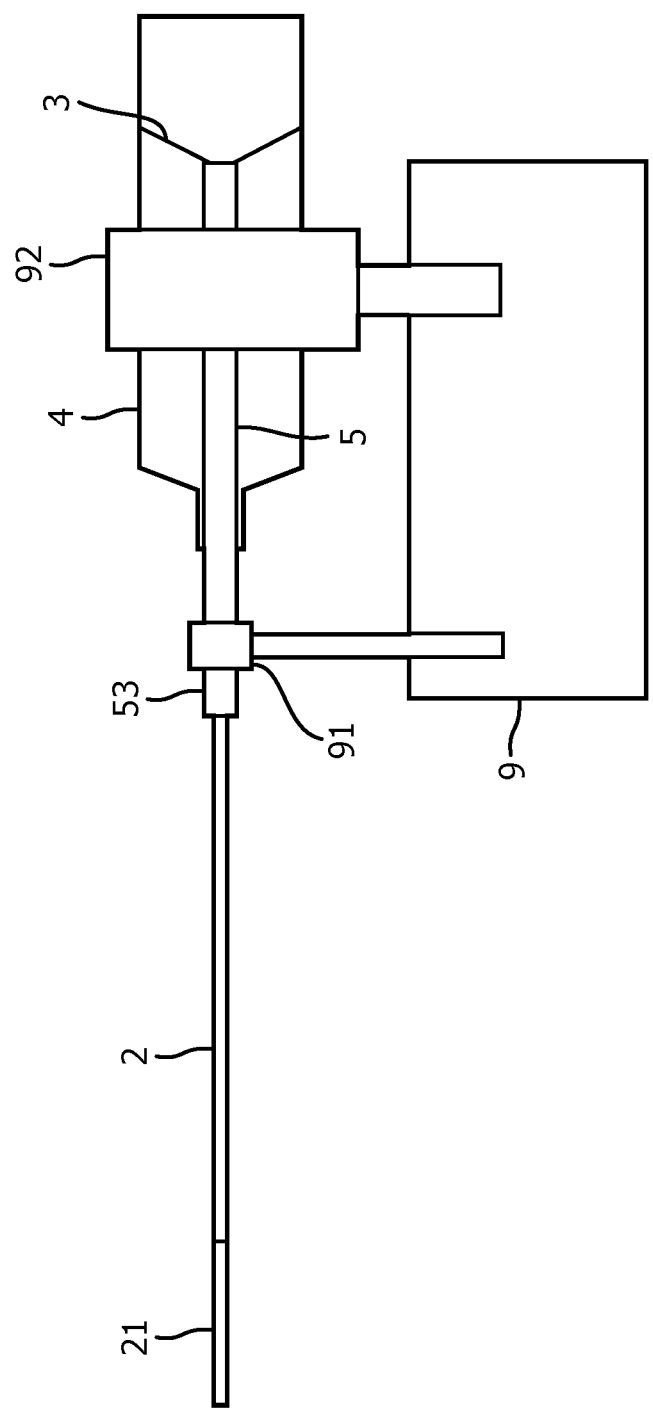
FIG. 6 is a schematic and exemplary illustration of a system for robotic control of the device according to the invention.

FIG. 6 illustrates an apparatus 9 for robotic manipulation of the device 1. The apparatus comprises two arms 91, 92 configured for clasping the control organ and the grip for influencing the angular displacement of the rigid elongate member. In FIG. 6 the control organ is the distal extension 53 of the rigid elongate member 5. In alternative embodiment, such as illustrated in FIG. 1A, the control organ 51 may be located on the outer side of the grip structure 4. The arms 91, 92 provide movement for relative motion of the control organ with respect to the grip based on a preprogrammed roadmap.

Figure 7:
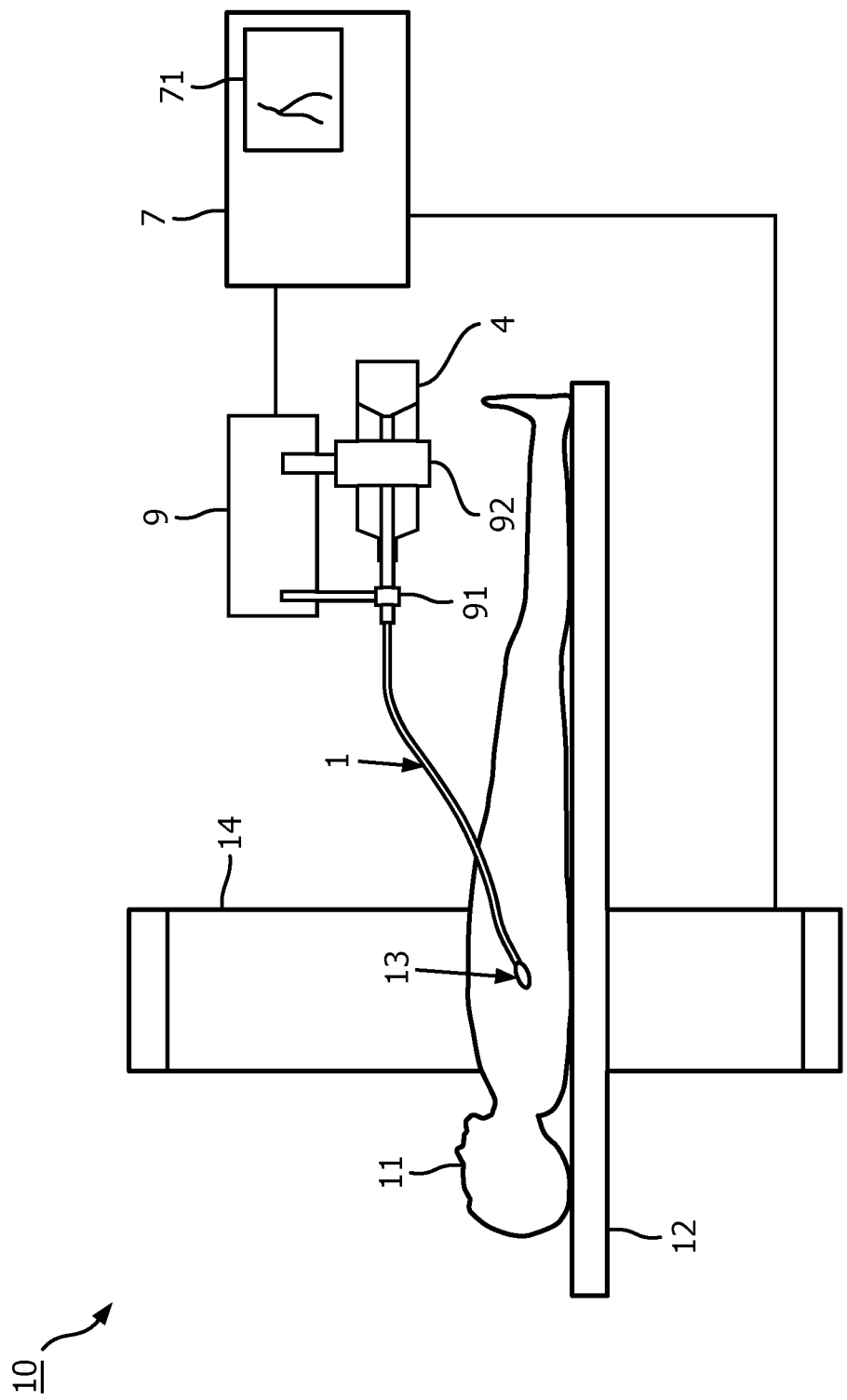
FIG. 7 is a schematic and exemplary illustration of the system for robotic control of the device based on predetermined roadmap.

The apparatus 9 may be part of a system used in an interventional room in clinical practice, as schematically illustrated in FIG. 7. The system 10 comprises an extracorporeal imaging apparatus 14 for imaging anatomical structures of a patient 11 placed on an interventional bed 12. Any of the well-established imaging techniques may be used by the extracorporeal imaging apparatus, such as: RA, MRA or UI. For the respective imaging modalities also contrast agents are available for enhancing the features of the blood vessel system, for instance radiological contrast agent for RA, a gadolinium-based substance for MRA, echogenic contrast agent comprising microbubbles for extracorporeal UI. The information of the vessel system and/or the anatomical organ is received by the external processing unit 7, which may generate an output of the received information for visualization on a display 71. The external processing unit is configured to allow generation of a roadmap based on the received extracorporeal imaging information either by interaction of a physician or by automatic segmentation of the vessel system and/or the anatomical organ upon a selection of a clinical procedure. The physician may select via an interface coupled to the external processing unit an entry point into the vascular system and a target location 13 within the body of the patient 11, where the distal end of the device needs to be navigated, based on the provided extracorporeal image. Alternatively or additionally, the physician may define a treatment scheme of an organ, e.g. ablation sites within a chamber of the heart. The roadmap is transmitted from the external processing unit through wired or wireless communication to the robotic manipulation apparatus 9. The robotic manipulation apparatus computes the relative movements of the two arms 91 and 92 with respect to each other in order to provide the appropriate sequence of movements to the control organ and the grip of the device in order to complete the actions predetermined by the physician or by the automatic segmentation according to the roadmap. The robotic manipulation apparatus 9 may be provided with a translation stage for advancing the device 1 within the vasculature toward the target location, while simultaneous and sequential relative movements of the two arms provide steering of the distal end of the device. In this manner the steering of the distal portion of the elongate body can be automated, which is beneficial for navigation through a vessel structure to a target location for diagnostic purposes such as for diagnostic of stenosis in coronary or cerebrovascular vessel, or for treatment of an anatomical organ such as a heart wherein multiple ablations on subsequent sites are performed for treating cardiac arrhythmia.

In the claims, the word "comprising" does not exclude other elements or steps, and the indefinite article "a" or "an" does not exclude a plurality.

Any reference signs in the claims should not be construed as limiting the scope.

The invention claimed is:

1. An elongate device with a bendable distal end, comprising:
    an elongate body having a distal portion at the bendable distal end, a proximal portion and a lumen;
    a pull-wire located within the lumen, the pull-wire extending from the distal portion of the elongate body to the proximal portion of the elongate body and fixedly attached to the distal portion of the elongate body so that tension on the pull-wire causes the bendable distal end to bend;
    a grip structure connected to the proximal portion of the elongate body, wherein the grip structure comprises a hollow interior;
    a rigid elongate member fixedly attached to a distal portion of the grip structure and forming a pathway for the pull-wire, wherein the pull-wire extends proximally through the rigid elongate member and is fixedly attached at an eccentric angle to an interior portion of a wall of the grip structure, wherein the rigid elongate member is configured for angular displacement within the hollow interior of the grip structure that places tension on the pull wire;
    a control organ extending through the wall in the grip structure to the rigid elongate member, wherein an external pressure applied to the control organ influences the angular displacement of the rigid elongate member, thereby producing tension on the pull-wire and bending the bendable distal end.

2. The device according to claim 1, comprising a second pull-wire extending from the distal end of the elongate body through the rigid elongate member and rigidly fixed at a second eccentric angle to the interior portion of the wall in the grip structure, wherein the second pull-wire is located on an opposite side of a diagonal through the longitudinal axis of the elongate body from the pull-wire, and wherein the rigid elongate member is configured for angular displacement in a longitudinal plane comprising its longitudinal axis that produces bending in the bendable distal end in at least two different directions in response to pressure applied to the pull-wire and the second pull-wire.

3. The device according to claim 2, comprising at least one additional pull-wire extending from the distal end of the elongate body through the rigid elongate member and rigidly fixed at a third eccentric angle to the interior portion of the wall in the grip structure, wherein the pull-wire, the second pull-wire and the at least one additional pull-wire are all located equidistant from each other and equidistant from the longitudinal axis of the elongate body in a plane transversal to the longitudinal axis of the elongate body, and wherein pressure applied to the rigid elongate member produces bending in the bendable distal end in at least three different directions in response to pressure applied to the pull-wire, the second pull-wire and the at least one additional pull-wire.

4. The device according to claim 1, wherein the diameter of the pull-wire is in the range of 0.025-0.15 mm and a diameter of the elongate body is in the range of 0.55-1.5 mm.

5. The device according to claim 1, wherein the distal portion of the grip structure extends along a predetermined length of the rigid elongate member, the distal portion of the grip structure is configured to allow movement of the distal portion of the grip structure with respect to a proximal main body of the grip structure.

6. The device according to claim 5, wherein an inner cross section of the distal portion of the grip structure is configured for press-fitting the rigid elongate member and wherein an inner cross section of the proximal main body is at least three times the inner cross section of the distal portion of the grip structure.

7. The device according to claim 1, wherein the control organ is connected to the rigid elongate member and is operable from an outer side of the grip structure.

8. The device according to claim 1, wherein the distal portion of the elongate body comprises a sensor connected to a control unit located within the grip structure.

9. The device according to claim 8, wherein the control unit is configured for wireless communication with an external processing unit for transmitting measurement information from the sensor to the external processing unit.

10. The device according to claim 1, wherein the grip structure, the elongate body, a connection of the elongate body to the grip structure and to the rigid elongate member are configured to form a closed system whereby the device is leak-tight to liquids.

11. The device according to claim 1, comprising a friction disc assembly configured to immobilize the rigid elongate member with respect to the grip structure in a selected position.

12. The device according to claim 11, wherein the friction disc assembly comprises:
    a friction disc fixedly attached to a proximal portion of the rigid elongate member;
    a first structure fixed within the grip structure at a position proximal to the friction disc;
    a second structure movable within the grip structure and located distal to the friction disc;
    a second control organ connected to the second structure and operable from an outer side of the grip structure.

13. A system comprising the device according to claim 1 and an apparatus configured to:
    clasp the grip structure and the control organ; and
    provide relative movement of the control organ with respect to the grip structure based on a predetermined roadmap.

14. The system according to claim 13, further comprising an extracorporeal imaging unit and wherein the predetermined roadmap is based on extracorporeal imaging of a vessel system and/or an anatomical organ in a body.

* * * * *